(12) United States Patent
Lumsdaine et al.

(10) Patent No.: US 11,793,680 B2
(45) Date of Patent: Oct. 24, 2023

(54) COMPOUND (MULTI-LAYER) WATERPROOF BANDAGE

(71) Applicants: Anne J. Lumsdaine, Palo Alto, CA (US); Edward James L. Ross, Palo Alto, CA (US)

(72) Inventors: Anne J. Lumsdaine, Palo Alto, CA (US); Edward James L. Ross, Palo Alto, CA (US)

( * ) Notice: Subject to any disclaimer, the term of this patent is extended or adjusted under 35 U.S.C. 154(b) by 187 days.

(21) Appl. No.: 17/200,741

(22) Filed: Mar. 12, 2021

(65) Prior Publication Data
US 2021/0282978 A1 Sep. 16, 2021

Related U.S. Application Data

(60) Provisional application No. 62/988,805, filed on Mar. 12, 2020.

(51) Int. Cl.
*A61F 13/00* (2006.01)
*A61F 13/04* (2006.01)
*A61F 13/02* (2006.01)

(52) U.S. Cl.
CPC ........ *A61F 13/041* (2013.01); *A61F 13/0206* (2013.01); *A61F 2013/00582* (2013.01);
(Continued)

(58) Field of Classification Search
USPC .................................. 602/3, 75, 79
See application file for complete search history.

(56) References Cited

U.S. PATENT DOCUMENTS 3,645,825 A * 2/1972 Gaunt .................... B65B 7/164
53/329.3
3,645,835 A 2/1972 Hodgson
(Continued)

FOREIGN PATENT DOCUMENTS

GB 1301101 A * 12/1972 ............. A61L 15/18
GB 1301101 A 12/1972
(Continued)

OTHER PUBLICATIONS

"Few Waterproof Bandages Make the Cut." Product Reviews and Ratings—ConsumerReports, Consumer Reports, Nov. 2010, www.consumerreports.org/cro/2012/12/fewwaterproof-bandages-make-the-cut/index.htm.
(Continued)

*Primary Examiner* — Kim M Lewis
(74) *Attorney, Agent, or Firm* — IP Clinic at Lincoln Law School of San Jose (57) ABSTRACT

One embodiment of a waterproof bandage for reliably protecting sensitive sites from water intrusion, despite potential flaws in the seal to skin, comprises three major components: the inner bandage, comprising an absorbent layer (1) and a waterproof layer (2); the outer bandage, comprising an absorbent layer (3) and a waterproof layer (4); and an adhesive layer (5) binding the waterproof layer of the inner bandage (2) and the absorbent layer of the outer bandage (3) together. When properly sized, registered and bonded, the outer absorbent layer (3) functions to wick away and to prevent any water that may penetrate the outer waterproof layer (4) from breaching or damaging the inner bandage. The waterproof bandage can be configured in various sizes as a bandage (FIG. 1), or as a sleeve-like cover for a protected site on hands, arms, feet, legs, and other parts of the body (FIGS. 3 and 4).

19 Claims, 4 Drawing Sheets

(52) U.S. Cl.
CPC ............... *A61F 2013/00604* (2013.01); *A61F 2013/00731* (2013.01)

(56) References Cited

U.S. PATENT DOCUMENTS

| | | | |
|---|---|---|---|
| 3,741,203 | A | 6/1973 | Liman |
| 3,888,247 | A * | 6/1975 | Stenvall ............... A61F 13/0203 D24/189 |
| 4,341,207 | A * | 7/1982 | Steer .................. A61F 13/0213 602/56 |
| 4,363,317 | A | 12/1982 | Broucek |
| 4,499,896 | A | 2/1985 | Heinecke |
| 4,562,834 | A | 1/1986 | Bates et al. |
| 4,595,001 | A | 6/1986 | Potter et al. |
| 4,911,151 | A | 3/1990 | Rankin et al. |
| 4,926,851 | A | 5/1990 | Bulley |
| 4,969,880 | A | 11/1990 | Zamierowski |
| 5,109,874 | A | 5/1992 | Bellingham et al. |
| 5,261,893 | A | 11/1993 | Zamierowski |
| 5,592,953 | A | 1/1997 | Delao |
| 5,633,010 | A | 5/1997 | Chen |
| 5,817,038 | A * | 10/1998 | Orange ................. A61F 13/041 602/62 |
| 5,823,977 | A * | 10/1998 | Dalyea .................. A61F 15/004 602/3 |
| D409,754 | S | 5/1999 | Dunshee et al. |
| 5,933,863 | A | 8/1999 | Monsue |
| 6,284,941 | B1 | 9/2001 | Cox et al. |
| D454,955 | S | 3/2002 | Dunshee et al. |
| 6,399,852 | B1 | 6/2002 | Barron |
| 6,450,982 | B1 | 9/2002 | Peterson |
| 6,506,175 | B1 | 1/2003 | Goldstein |
| 6,730,053 | B1 | 5/2004 | Bodenschatz et al. |
| D495,419 | S | 8/2004 | Dunshee |
| 6,863,960 | B2 | 3/2005 | Curro et al. |
| 7,022,095 | B2 | 4/2006 | Schneider |
| 7,048,708 | B2 | 5/2006 | Evans et al. |
| D551,352 | S | 9/2007 | Frangi |
| 7,338,482 | B2 | 3/2008 | Lockwood et al. |
| 7,351,217 | B2 | 4/2008 | Scherpenborg |
| D571,923 | S | 6/2008 | Roberts |
| D601,706 | S | 10/2009 | Bauerfeind et al. |
| D608,896 | S | 1/2010 | Arbesman et al. |
| D627,071 | S | 11/2010 | Sevigny |
| 7,857,777 | B2 | 12/2010 | Larson et al. |
| 8,062,447 | B2 | 11/2011 | Wei |
| 8,137,294 | B2 | 3/2012 | Baschnagel |
| 8,168,848 | B2 | 5/2012 | Lockwood et al. |
| 8,240,472 | B2 | 8/2012 | Khan |
| D669,179 | S | 10/2012 | Fisher |
| D673,279 | S | 12/2012 | Huttner |
| 8,372,051 | B2 | 2/2013 | Scholz et al. |
| 8,403,873 | B2 | 3/2013 | Schuren et al. |
| 8,529,481 | B1 * | 9/2013 | Lois .................. A41D 13/0005 602/3 |
| 8,708,938 | B2 | 4/2014 | Evans et al. |
| 8,784,793 | B2 | 7/2014 | Salamone et al. |
| 8,884,094 | B2 | 11/2014 | Lockwood et al. |
| D721,975 | S | 2/2015 | Arefieg |
| D737,453 | S | 8/2015 | Gergely et al. |
| 9,271,877 | B2 | 3/2016 | Mouton |
| D774,201 | S | 12/2016 | Gutierrez et al. |
| 9,592,160 | B2 | 3/2017 | Bacon et al. |
| 9,649,227 | B2 | 5/2017 | Vollbrecht |
| 9,861,531 | B2 | 1/2018 | Cobanoglu et al. |
| D843,588 | S | 3/2019 | Slowey |
| D846,129 | S | 4/2019 | Rossi |
| 10,285,867 | B2 | 5/2019 | Rapp et al. |
| D862,711 | S | 10/2019 | Rossi et al. |
| 10,575,990 | B2 | 3/2020 | Etchells et al. |
| D890,352 | S | 7/2020 | Dechow |
| 10,765,353 | B2 | 9/2020 | Biederman et al. |
| 10,952,907 | B1 | 3/2021 | Carver |
| 11,013,639 | B1 | 5/2021 | Temkin et al. |
| D944,404 | S | 2/2022 | Rokitta |
| D959,680 | S | 8/2022 | Caneppele et al. |
| 2004/0186403 | A1 | 9/2004 | Bodenschatz et al. |
| 2006/0074367 | A1 | 4/2006 | Palma |
| 2006/0143767 | A1 | 7/2006 | Yang et al. |
| 2013/0060217 | A1 | 3/2013 | Mouton |
| 2014/0121649 | A1 | 5/2014 | Calco |
| 2015/0072966 | A1 | 3/2015 | Boykin, Jr. et al. |
| 2018/0221627 | A1 | 8/2018 | Wilborn et al. |
| 2019/0183672 | A1 * | 6/2019 | Ellerbrake-Sadler ....................... A61F 13/022 |
| 2020/0038252 | A1 | 2/2020 | Spiro |

FOREIGN PATENT DOCUMENTS

| | | |
|---|---|---|
| WO | 2006065854 A2 | 6/2006 |
| WO | 2020028050 A1 | 2/2020 |

OTHER PUBLICATIONS

"Surgical Site Infection: Prevention and Treatment of Surgical Site Infection." Surgical SiteInfection: Prevention and Treatment of Surgical Site Infection, National Collaborating Centrefor Women 's and Children's Health (UK), London: RCOG Press; Oct. 2008. (NICEClinical Guidelines, No. 74.).

Altman, Sanford. "Showering with Central Venous Catheters: Experience Using the CD-1000 Composite Dressing." The Canadian Journal of Chemical Engineering, Wiley-Blackwell, May 9, 2006, onlinelibrary.wiley.com/doi/full/10.1002/dat.20022.

Austin, Jennifer Jensen, and Bharat Patel. "Considerations for Adhesion to Skin." Considerations for Adhesion to Skin—1dffbc30255204f2f691524588403c31ec74.Pdf, Johnson &Johnson Consumer Products Company, pdfs.semanticscholar.org/e84a/1dffbc30255204f2f691524588403c31ec74.pdf.

Carter, D.L., Shah, D.O. The role of surface tension on the residual water content of fabrics. JSurfact Deterg 8, 91-94 (2005). https://citeseerx.ist.psu.edu/viewdoc/download?doi=10.1.1.631.6106&rep=rep1&type=pdf.

Cruz, Juliana, et al. "Study of Moisture Absorption Characteristics of Cotton Terry TowelFabrics." Procedia Engineering, vol. 200, Jun. 2017, pp. 389-398., doi: 10.1016/j.proeng.2017.07.055.

Downie, F, et al. "Barrier Dressings in Surgical Site Infection Prevention Strategies." CurrentNeurology and Neuroscience Reports., U.S. National Library of Medicine,www.ncbi.nlm.nih.gov/pubmed/21072011.

Ling, Et al. "APSIC Guide for Prevention of Central Line Associated Bloodstream Infections(CLABSI)." APSIC Guide for Prevention of Central Line Associated Bloodstream Infections(CLABSI), NIH, May 4, 2016, www.ncbi.nlm.nih.gov/pmc/articles/PMC4857414/.

Web Archived Page, "Band-aid brand hydro seal large bandages", Archived May 5, 2020, retrieved from Internet Archive Wayback Machine.

Web Archived Site, "DrySee" Archived Dec. 29, 2020, found at https://web.archive.org/web/20201229055444/https://drysee.com/.

Web Archived Site, "Nexcare," Archived Oct. 21, 2020, found at https://web.archive.org/web/20201021072756/https://www.nexcare.com/3M/en_US/nexcare/.

* cited by examiner

COMPOUND (MULTI-LAYER) WATERPROOF BANDAGE

CROSS-REFERENCE TO RELATED APPLICATION

This application claims the benefit of provisional patent application Ser. No. 62/988,805, filed 2020 Mar. 12 by the present inventors, which is incorporated by reference in its entirety.

FIELD OF INVENTION

The present invention pertains to medical bandages, in particular to waterproof bandages or dressings to protect wounds, sensitive sites or medical dressings.

BACKGROUND

Keeping cuts, scrapes, stitches, small burns, dressings over peripheral and other catheter insertion sites, cardiac ports, casts, and other wounds or sensitive sites dry and/or clean facilitates healing and prevents infection. Keeping sterile dressings in good condition between dressing changes and protecting attached medical devices or transdermal drug delivery patches, for example, facilitates successful treatment and reduces costs and disruptions to care. However, it is difficult to keep such sites dry and clean during ordinary life activities and especially when showering or bathing.

In order to protect such sites, conventional waterproof bandages and coverings to protect dressings for bathing are designed to create a full adhesive seal to skin or other surfaces around the protected site using waterproof materials, which keep water and other contaminants from the site and keep the site dry and clean. Pressure is an alternative method of creating a seal to exclude water, for example, a tight opening to a waterproof cover to protect casts.

Commercially available bandages and shower protection systems leak despite being marketed as "water resistant" or "waterproof". We have noticed that waterproof bandages' ability to keep out water is dependent on the integrity of the adhesive or pressure seal to the skin which is difficult to make perfect.

We have further noticed that almost any small flaw in a bandage seal to the skin can result in a significant leak during bathing or showering because of capillary action. Additionally, we have observed that sweat forming under protective waterproof coverings that may be used to protect wounds or medical dressings during daily activities or bathing, can affect the wound or dressing underneath similarly to water intrusion from leaks. We have also observed that surfactants used in bathing reduce surface tension of water, allowing it to more readily wick into small flaws in adhesive seals. Online-published consumer testing of waterproof bandages missed the need for real-world testing conditions with surfactants and thus missing a major contributor to leaks.

Leaks resulting from bandage seal flaws compromise the hygiene of wounds or sensitive sites, and put patients at risk of infection. Water leaks and sweat further compromise the integrity of said seals. This is especially a concern when protecting medical dressings or other devices that are used over extended periods, such as peripheral catheter insertion site dressings, where exposure of sterile dressings to water from bathing may result in peeling, and require premature change by a nurse to avoid risking site infection or damage to the line.

Waterproof dressings on the market have relied on increasing adhesive strength or bandage pressure to create a kind of "perfect" seal. From our observation, in the presence of even tiny imperfections, leaks are almost inevitable, and a reliably perfect seal to skin or other surfaces is very difficult to achieve. Many commercial bandages leak, as the presence of rough skin texture, skin oils, sweat, hair, surfactant residue from washing, flawed application by the user, and other irregularities make complete seals difficult to achieve. Although products have been made to increase bandage adhesive strength and/or add pressure to reduce leaking, these strategies don't eliminate leaking and can be uncomfortable to the wearer, difficult to remove, and have the potential to damage the sensitives sites they are intended to protect.

In one embodiment, a waterproof bandage system used to keep wounds, sensitive sites, and other dressing or devices free from water intrusion while the bandage is exposed to water, especially during showering or bathing. A water proof bandage system comprising an inner bandage component used to keep wounds and sensitive sites free from water intrusion while the bandage is exposed to water, especially during showering or bathing, comprising at least one waterproof layer that can be adhered to a surface. A waterproof bandage system of at least one outer bandage component comprising an absorbent layer and a waterproof layer that can be adhered to a surface and the waterproof layer of said inner bandage being bonded in a parallel orientation to the undersurface of the absorbent layer of the outer bandage with an adhesive bonding layer or other bonding method.

In another embodiment, a bandage or wound dressing according to claim 1, wherein the waterproof layer of said inner bandage is overlapped on one or more sides by the absorbent layer of said outer bandage.

In a third embodiment, a bandage or dressing according the claim 1, wherein the inner bandage comprises an absorbent layer to absorb fluid, including but not limited to sweat and blood, away from the wound or sensitive site below. A bandage or dressing according to claim 1, wherein there is a waterproof layer that can be adhered to a surface.

In a fourth embodiment, a bandage or wound dressing according to claim 1 and claim 3 wherein the shape of the inner bandage and outer bandage components and their comprising layers are predominantly planar and are predominantly selected from (but are not limited to) geometric and organic shapes, including polygons, circles, rings, and ovals, or are predominately tubular.

In a fifth embodiment, a bandage or wound dressing according to claims 1, 3, and 4, wherein the bandage contains a lengthwise slit in one or more layers, and is wrapped onto the appendage or surface.

In a sixth embodiment, a bandage or wound dressing according to claims 1, 3, and 4, wherein an end cap is attached to the open end of the bandage, and may be made of the same comprising layers of the bandage, or one or more layers of a substantially flexible adhesive or film.

In a seventh embodiment, a bandage or wound dressing according to claim 1 and claim 3, wherein the outer bandage and bonding layer or layers may be separated from the inner bandage and replaced, applied separately, or removed entirely when not needed.

In an eighth embodiment, a bandage or wound dressing according to claim 1, wherein the component layers of the inner bandage and outer bandage are made of substantially biodegradable materials.

In a ninth embodiment, a bandage or wound dressing according to claim 1, wherein the waterproof layers of the bandage are made of substantially non-rigid material or film.

In a tenth embodiment, a bandage or wound dressing according to claim 1, wherein the absorbent layers are predominately made of a substantially absorbent material, such as fiber or cloth.

In an eleventh embodiment, a bandage or wound dressing according to claim 1, wherein the inner bandage and outer bandage components and their comprising layers are made from substantially washable or reusable materials.

In a twelfth embodiment, a bandage or wound dressing according to claims 1, 4, 7, and 11, wherein the outer absorbent layer is held adjacent to the inner waterproof layer or protected site dressing using a tightening or securing mechanism.

In a thirteenth embodiment, a bandage according to claims 1, 4, 7, 11, and 12, wherein the outer waterproof layer may be attached using a mechanism to tightly secure the outer waterproof layer and covered layers to the application surface.

In a fourteenth embodiment, a method of absorbing and holding water that infiltrates a first waterproof dressing or cover covering a second waterproof or water-resistant barrier, including but not limited to a medical dressing or cast, to prevent further infiltration of said water through the second waterproof or water-resistant barrier or barriers.

In a fifteenth embodiment, the method according to claim 14, wherein said water is absorbed with an absorbent material integrated into the first dressing, sized and positioned such that the edges of the absorbent material may overlap the edges of the second waterproof or water-resistant barrier or barriers on one or more sides.

In a sixteenth embodiment, the method according to claims 14 and 15, wherein the integrated absorbent material is adhered to the other waterproof or water-resistant barrier or barriers.

In a seventeenth embodiment, an apparatus comprising a first bandage component comprising a first waterproof layer having a first waterproof layer shape, a second bandage component comprising a second waterproof layer having a second waterproof layer shape, a third bandage component comprising a first absorbent layer having a first absorbent layer shape, a fourth bandage component comprising a second absorbent layer having a second absorbent layer shape, wherein the second waterproof layer having the second waterproof layer shape is disposed over and overlaps the second absorbent layer having the second absorbent layer shape, which in turn, is disposed over and overlaps the first waterproof layer having the first waterproof layer shape, which in turn, is disposed over and overlaps the first absorbent layer having the first absorbent layer shape. An apparatus comprising a bonding layer located between the first waterproof layer having the first waterproof layer shape and the second absorbent layer having the second absorbent layer shape, wherein the second absorbent layer having the second absorbent layer shape is adhered to the first waterproof layer having the first waterproof layer shape.

In an eighteenth embodiment, the apparatus of claim 1, wherein the first absorbent layer absorbs a fluid including at least one of water, sweat or blood.

In a nineteenth embodiment, the apparatus of claim 1, wherein at least one of the first waterproof layer shape, the second waterproof layer shape, the first absorbent layer shape, or the second absorbent layer shape comprises at least one of: geometric or organic shapes, polygons, circles, rings, ovals or shapes that are tubular.

In a twentieth embodiment, the apparatus of claim 1, wherein at least one of the first waterproof layer, the second waterproof layer, the first absorbent layer, or the second absorbent layer has a lengthwise slit.

In a twenty-first embodiment, the apparatus of claim 1, wherein one or more of the first bandage component, the second bandage component, the third bandage component, or the fourth bandage component is wrapped around an appendage.

In a twenty-second embodiment, the apparatus of claim 5, wherein one or more of the first bandage component, the second bandage component, the third bandage component, or the fourth bandage component has an end cap.

In a twenty-third embodiment, the apparatus of claim 6, wherein the end cap is made of a waterproof material.

In a twenty-fourth embodiment, the apparatus of claim 6, wherein the end cap is made of the same materials as at least one of the first bandage component, the second bandage component, the third bandage component, or the fourth bandage component.

In a twenty-fifth embodiment, the apparatus of claim 5, wherein one or more of the first bandage component, the second bandage component, the third bandage component, or the fourth bandage component is held in place using a tightening or securing mechanism.

In a twenty-sixth embodiment, the apparatus of claim 1, wherein at least one of the first waterproof layer, the second waterproof layer, the first absorbent layer, or the second absorbent layer is configured to be replaced.

In a twenty-seventh embodiment, the apparatus of claim 1, wherein at least one of the first waterproof layer, the second waterproof layer, the first absorbent layer, or the second absorbent layer is made of a at least one of a biodegradable material, a non-rigid material, or a non-rigid film.

In a twenty-eighth embodiment, the apparatus of claim 1, wherein one or more additional outer bandage layers may be applied over the second bandage component comprising the second waterproof layer.

In a twenty-ninth embodiment, the apparatus of claim 1, wherein at least one of the first absorbent layer or the second absorbent layer is made of fiber or cloth.

In a thirtieth embodiment, the apparatus of claim 1, wherein the bonding layer includes at least one of: an adhesive, a non-adhesive, a full seal, a pressure seal, a non-full seal, one or more strips of adhesive or of the non-adhesive, one or more adhesive strips, or one or more compression straps.

In a thirty-first embodiment, the apparatus of claim 1, wherein a combination of the bonding layer and the second absorbent layer are configured to prevent a liquid intrusion.

In a thirty-second embodiment, the apparatus of claim 1, wherein the first waterproof layer and the second waterproof layer each include an adhesive.

In a thirty-third embodiment, the apparatus of claim 1, wherein at least one of the second absorbent layer is used to absorb or attract a liquid such that the liquid does not infiltrate the first bandage component comprising the first waterproof layer or, in some cases the second absorbent layer protects the first bandage component comprising the first waterproof layer after the second absorbent layer is saturated.

In a thirty-fourth embodiment, the apparatus of claim 1, wherein at least one of the second waterproof layer or the second absorbent layer is made of a washable or reusable material.

In a thirty-fifth embodiment, a method for manufacture of an apparatus, comprising providing a first bandage component comprising a first waterproof layer having a first waterproof layer shape.

Further disclosed herein is a method for manufacture of an apparatus, comprising steps of: providing a first bandage component comprising a first waterproof layer having a first waterproof layer shape; providing a second bandage component comprising a second waterproof layer having a second waterproof layer shape; providing a third bandage component comprising a first absorbent layer having a first absorbent layer shape; providing a fourth bandage component comprising a second absorbent layer having a second absorbent layer shape; wherein the second waterproof layer having the second waterproof layer shape is disposed over and overlaps, at least in part, the second absorbent layer having the second absorbent layer shape, which in turn, is disposed over and overlaps, at least in part, the first waterproof layer having the first waterproof layer shape, which in turn, is disposed over and overlaps, at least in part, the first absorbent layer having the first absorbent layer shape; providing a bonding layer located between the first waterproof layer having the first waterproof layer shape and the second absorbent layer having the second absorbent layer shape, wherein the second absorbent layer having the second absorbent layer shape is adhered to the first waterproof layer having the first waterproof layer shape.

Further disclosed herein is an apparatus comprising: a first bandage component comprising a first waterproof layer having a first waterproof layer shape; a second bandage component comprising a second waterproof layer having a second waterproof layer shape; a third bandage component comprising a first absorbent layer having a first absorbent layer shape; wherein the second waterproof layer having the second waterproof layer shape is disposed over and overlaps the first absorbent layer having the first absorbent layer shape, which in turn, is disposed over and overlaps the first waterproof layer having the first waterproof layer shape; a bonding layer located between the first waterproof layer having the first waterproof layer shape and the first absorbent layer having the first absorbent layer shape, wherein the first absorbent layer having the first absorbent layer shape is adhered to the first waterproof layer having the first waterproof layer shape; wherein the first waterproof layer having the first waterproof layer shape includes at least one of: a catheter line cover, a PICC line cover, a surface, or a bandage layer.

This problem was partially solved in narrow applications by the implementation of very large-area adhesive waterproof bandages made of thin materials that cause some flaws to collapse, but these had and still have significant problems, for example they are difficult to apply, expensive, and must adhere tightly to a large area. They are often used as longer-duration sterile medical dressings and thus in need of protection themselves during showering and many life activities to maintain their integrity.

Current shower protectors operate on the same principle of excluding water with a waterproof cover. Sweat underneath can undermine the adhesive seal of the dressings to be protected, especially at the edges, and any tiny flaw in the shower protector can result in leakage that compromises the integrity of the dressing underneath or even absorbs into the wound or sensitive site.

Therefore, a need exists in the field for a waterproof bandage capable of reliably keeping a sensitive site dry and/or clean during activities of daily life, bathing, showering or other exposure to wetness, despite the presence of flaws in the bandage seal. A further need exists for a bandage design that does not rely purely on pressure or adhesive strength to keep sites dry and/or clean, one that is capable of keeping such sites dry and/or undamaged even if the bandage seal is flawed or interrupted.

Our invention keeps sensitive sites dry without relying on perfect seals to the skin, thus representing an improvement to the state of the art.

DETAILED DESCRIPTION

The following disclosures provide descriptions and illustrations of several possible embodiments but should not be construed as limiting the scope of the embodiments. The scope of the embodiments should be determined from the appended claims.

Terminology used to describe the various aspects and embodiments disclosed below should be interpreted to have the same meaning as would be apparent to someone with a basic understanding of the present field. Interpretation of said terminology should be consistent with the context of the following embodiments and disclosures unless explicitly defined otherwise.

The term "waterproof bandage" as used herein refers to multiple embodiments wherein said bandage may be utilized in different capacities, including as a waterproof bandage, a waterproof or water-resistant cover to protect other dressings or bandages, a waterproof cast cover, a bandage or cover to protect against dirt, microbes, or liquids other than water, and additional capacities.

BRIEF SUMMARY

One embodiment consists of layers that provide protection from water intrusion: an inner bandage consisting of an absorbent material covered by a larger waterproof adhesive material, similar to a typical bandage for covering a wound, and an outer bandage, also consisting of an absorbent layer that overlaps and is bonded to the outer layer of the inner bandage in a manner that it absorbs water away from all edges of the inner bandage and is covered by a larger waterproof adhesive material that adheres to the skin.

The outer bandage provides protection from water intrusion via the waterproof covering and its adhesive seal to the skin, but more importantly, the absorbent material under the outer layer is designed and positioned so as to prevent leakage from infiltrating or affecting the inner waterproof covering even if the inner bandage and outer bandage seals to the skin are not perfect, and leakage into the outer bandage occurs. Even if said outer waterproof layer fails, the outer absorbent layer, if properly constructed, sized and positioned, prevents intrusion into the inner bandage and the protected site, and protects the integrity of the inner bandage seal, even if the outer absorbent layer becomes saturated and even if the inner bandage seal contains flaws.

DESCRIPTION OF THE DRAWINGS—FIGURES

Some embodiments of the present invention are illustrated as an example and are not limited by the figures of the accompanying drawings.

DRAWINGS—REFERENCE NUMBERS

1 Inner absorbent layer (layer 1)
2 Inner waterproof layer (layer 2)
3 Outer absorbent layer (layer 3)
4 Outer waterproof layer (layer 4)
5 Bonding layer (layer 5)
6 Skin or other surface the waterproof bandage is adhered to
7 Compression straps to secure tubular bandage components
8 Sealing strip for wrapped bandage
9 End cap or glove

Figure 1:
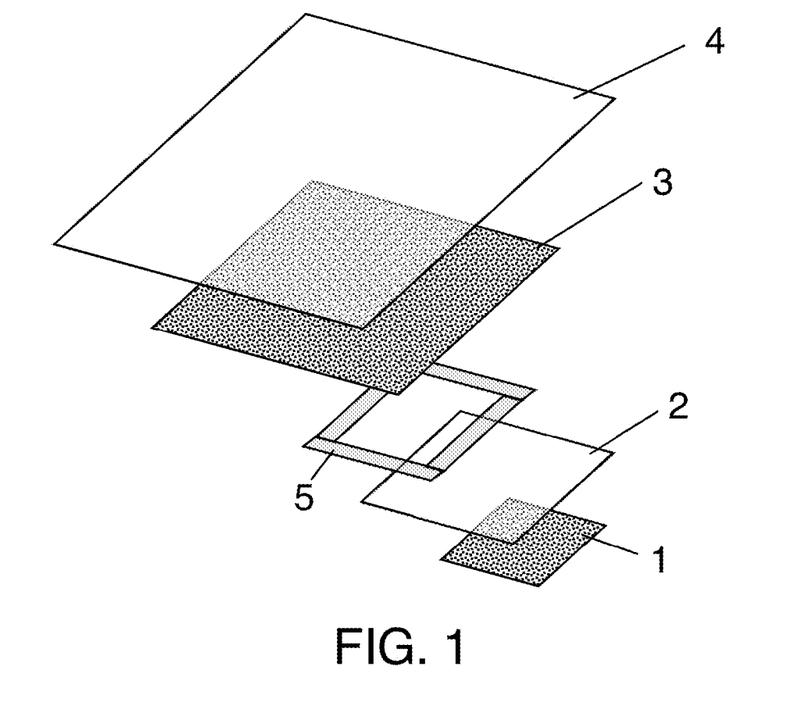
FIG. 1 depicts an exploded view of the first embodiment of the waterproof bandage.
Figure 2:
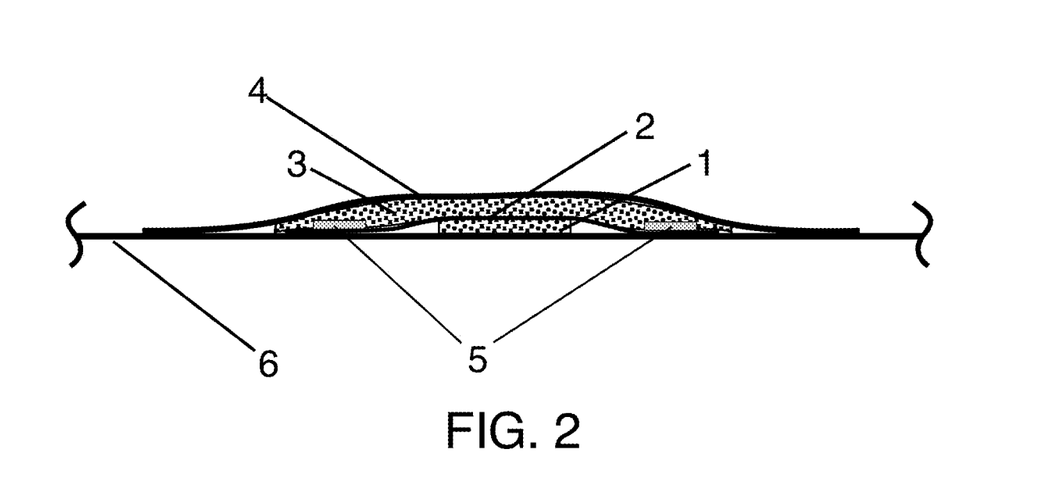
FIG. 2 depicts a section cut through the first embodiment.

DETAILED DESCRIPTION—FIGS. 1 AND 2—FIRST EMBODIMENT

FIG. 1 depicts an exploded view of elements that comprise the first embodiment of the waterproof bandage. Layers 1 and 2 comprise the inner bandage while layers 3 and 4 comprise the outer bandage. Layers 1 and 3 are made of substantially absorbent material, and layers 2 and 4 are made of substantially waterproof flexible material with adhesive on one or both sides. Layer 5, as shown, comprises an adhesive bonding layer used to bond layers 2 and 3 together. Adhesive layer 5 may alternatively comprise a different attachment method or agent.

FIG. 2 depicts a cross section through this embodiment of the waterproof bandage. In this embodiment, the outer bandage, comprised of layers 3 and 4, is placed over the inner bandage, comprised of layers 1 and 2, to protect the inner bandage from water intrusion and/or to protect the inner bandage seal from damage if water does intrude through layer 4. Layer 3 overlaps the edges of layer 2 to ensure that water is absorbed by layer 3, protecting the edges of layer 2 and potential seal flaws it may contain from wicking in leakage. Bonding layer 3 to layer 2 ensures their proper registration and proper functioning. In the present embodiment, adhesive layer 5 adheres the absorbent layer of the outer bandage to the waterproof layer of the inner bandage. In FIG. 2, adhesive layer 5 comprises strips of a non-liquid adhesive substance placed along the edges of layer 2. Adhesive layer 5 may alternatively comprise a different attachment method or agent or may be removed if needed. Adhering waterproof layer 2 to absorbent layer 3 ensures layer 3 remains in contact with layer 2, allowing absorbent layer 3 to absorb water away from the edges of waterproof layer 2. Reference number 6 indicates the surface of the skin of the user, or another surface to which the bandage is adhered.

FIG. 3—SECOND EMBODIMENT

Figure 3A:
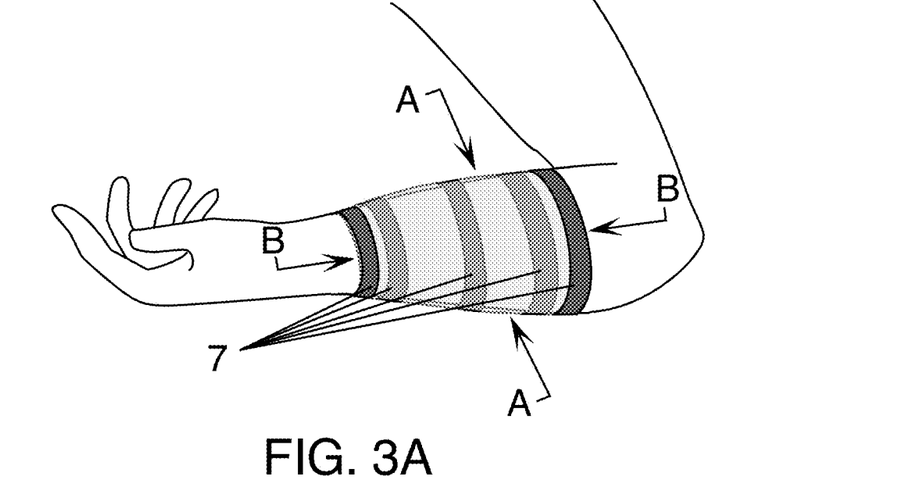
FIG. 3A depicts a second embodiment of the waterproof bandage encircling an arm and shows the directions of the section cuts in FIG. 3C and FIG. 3D.
Figure 3B:
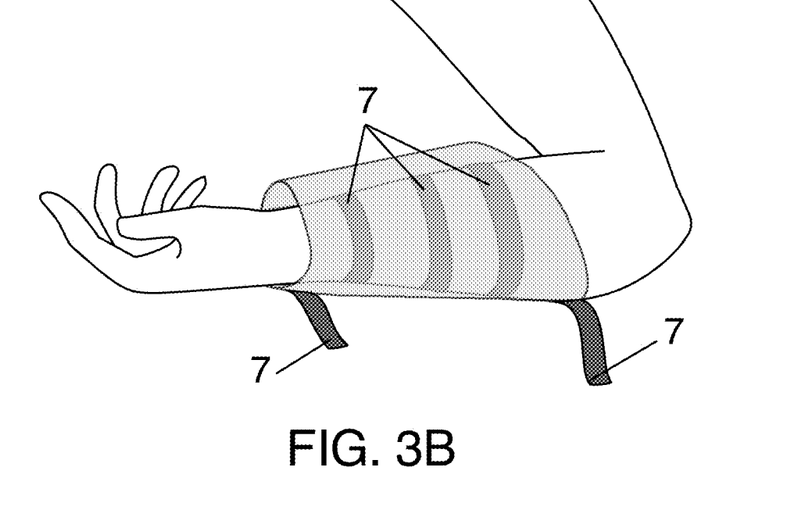
FIG. 3B depicts the second embodiment, wherein the straps securing the bandage have been loosened.

FIG. 3A depicts an assembled view of this embodiment attached to an appendage. In this embodiment, layers 1-5 are substantially tubular in shape when applied, and can be slid onto the appendage similarly to a sleeve as depicted in FIG. 3A and FIG. 3B. The section marked A-A is a perpendicular cross section of the waterproof bandage depicted in FIG. 3C, and the section marked B-B is a parallel cross section of the waterproof bandage depicted in FIG. 3D. Compression straps 7 may be made of an adhesive or non-adhesive material and securing mechanism to hold the components in their proper locations. Compression straps at the ends of outer waterproof layer 4 seal the ends from water intrusion. The straps under the outer waterproof layer 4 hold outer absorbent layer 3 in proper relative position relative to inner waterproof layer 2. This configuration of compression straps 7 is used as an example only, as there are other possible configurations. This embodiment can be configured to attach to any appendage or extremity including, but not limited to, arms, legs, fingers, or toes above, below, or across a joint. In this embodiment, layers 1-4 may be made of substantially reusable and washable materials, and/or substantially disposable materials.

FIG. 3B depicts the embodiments presented in FIG. 3A, but with the external compression straps 7 released.

Figure 3C:
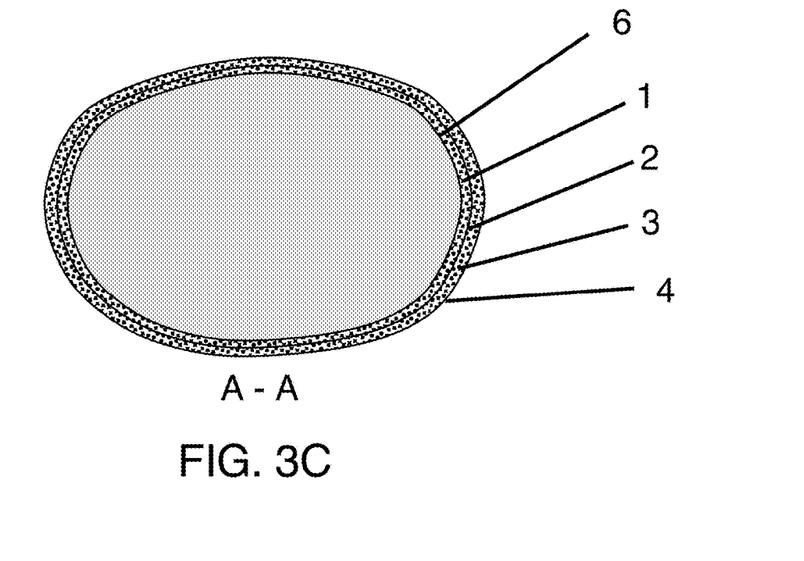
FIG. 3C is a cross-section through the embodiment depicted in FIG. 3A marked A-A.

FIG. 3C depicts a perpendicular cross section view A-A in FIG. 3A. Inner bandage layers 1 and 2 are stacked beneath the outer bandage layers 3 and 4. Layers 2 and 3 may be bonded together using an adhesive similar to layer 5 in FIG. 1, by some adhesive or non-adhesive bonding method, or be unbonded. Additionally, layers 1 and/or 2 may also be separated or applied separately from layers 3 and 4, for example, as in the case of an existing bandage being protected by layers 3 and 4.

Figure 3D:
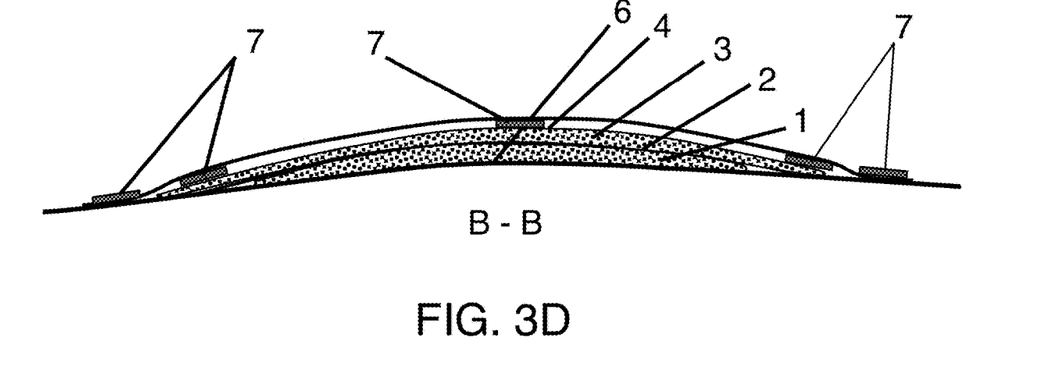
FIG. 3D is a cross-section through the embodiment depicted in FIG. 3A marked B-B.

FIG. 3D depicts a parallel cross section view B-B in FIG. 3A. As in FIG. 3C, the inner bandage layers 1 and 2 are stacked beneath outer bandage layers 3 and 4. In this depiction, layer 5 is not shown in this view, but layer 3 may still be bonded to layer 2 in order to ensure that layer 3 overlaps the edges of layer 2 at both ends of layer 2 or is otherwise properly registered. Compression pads 7 underneath outer waterproof layer 4 can be used to position waterproof layer 3 in proper proximity and alignment relative to inner waterproof layer 2.

Figure 4:
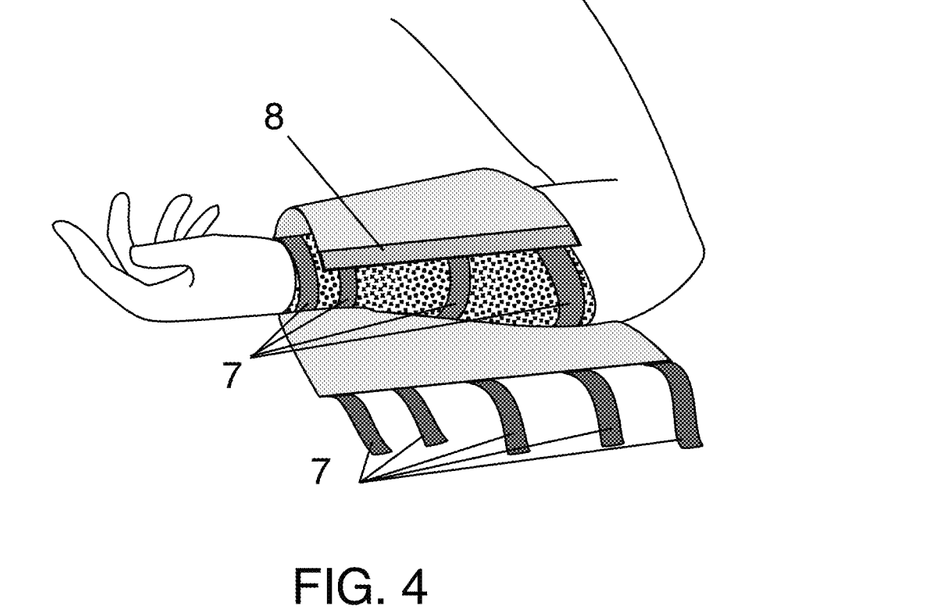
FIG. 4 depicts another embodiment similar to that depicted in FIG. 3A, wherein the waterproof bandage is of tubular shape with a longitudinal slit, and is wrapped around an appendage.
Figure 5:
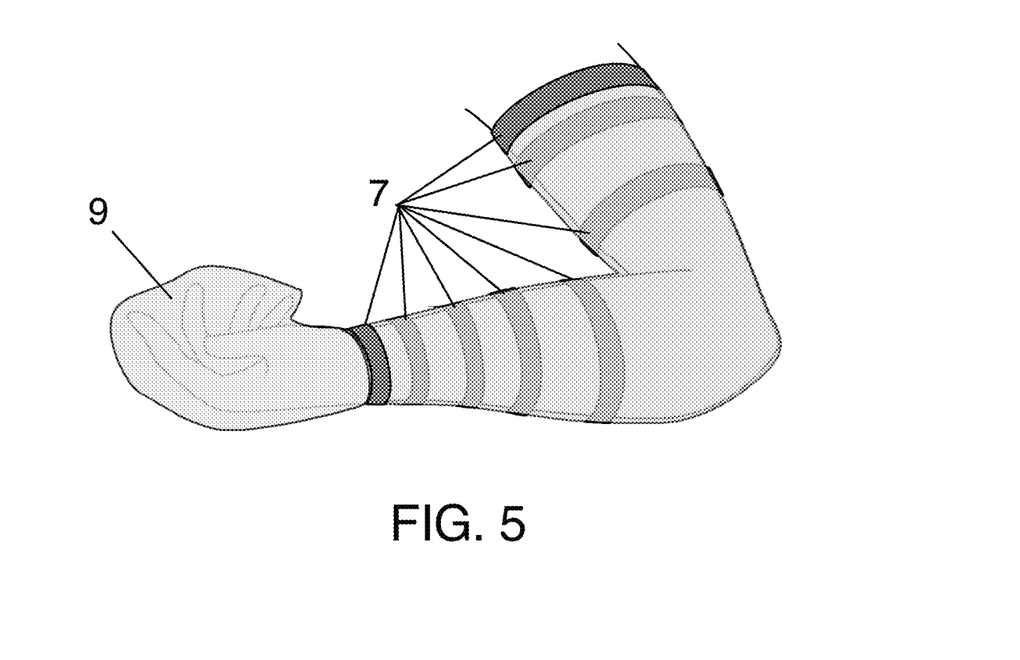
FIG. 5 depicts another embodiment encircling an arm past the joint with an attached end cap covering the hand.

FIG. 4-5—ADDITIONAL EMBODIMENTS

FIG. 4 depicts an alternate embodiment similar to the second embodiment depicted in FIG. 3A, with the addition of a longitudinal slit in outer waterproof layer 4 to allow an alternate method of applying layer 4. Sealing strip 8 is used to seal the slit in waterproof layer 4 when the bandage is applied. There may be more than one sealing strip present in similar embodiments where more than one layer contains a longitudinal slit.

FIG. 5 depicts an assembled view of an additional embodiment of the waterproof bandage. In this embodiment, the bandage is sized to cover an entire appendage including the joint. Additionally, end cap 9 has been placed over the end of the appendage. The cap may be an integral part of the waterproof bandage, or be attached after the bandage is applied. In this embodiment, end cap 9 may consist of a single waterproof layer, multiple waterproof layers, be fully integrated into the waterproof bandage and comprised of the same materials, or be removed entirely. In this embodiment, the bandage may include an adhesive or non-adhesive method to secure layers 1-4 to the appendage or surface. In this embodiment, the bandage may also be made of substantially reusable materials, and/or substantially disposable materials.

Testing:

Prototypes of the first embodiment depicted in FIG. 1 and FIG. 2 were subjected to testing during development by the second inventor on various appendages and body parts (arms, legs, trunk, and back) under shower conditions with soap and warm water for showers and a bath, each of approximately 15 minutes in length. Shower and bath testing was approved by an Institutional Review Board as exempt research; no disclosures were made to the Board.

In some tests, flaws were induced in the adhesive seals of the prototypes in both the inner bandage and outer bandage waterproof layers, breaching the full width from the outer edge of the adhesive layer to the absorbent layer. These were then tested both as full prototypes of the first embodiment and separately as individual components. After each test, each prototype or component was examined for evidence of water intrusion into all absorbent layers.

Although in full prototypes, flaws induced in outer bandage seals allowed water to enter "outer bandages", this water was absorbed by layer 3 and was prevented from entering into "inner bandages" (which also had induced flaws). This method of absorbing water away from the edges of layer 2 prevented water intrusion into sites protected by "inner bandages" and prevented water-induced damage to seals of said "inner bandages". Prototypes were found to have a 0% rate of water intrusion into protected sites even with induced flaws in both inner bandage and outer bandage waterproof layers, and even when, as in many of the tests, the absorbent layer of the outer bandage became very wet or saturated during testing.

When inner bandage and outer bandage components were tested separately rather than combined in a full prototype, the leakage rate was between 10% and 45% with no induced flaws in the adhesive seals. When flaws were induced in adhesive seals, leakage rates of separately tested inner bandage and outer bandage components increased to as high as 80%. The outer absorbent layer provided by absorbent layer 3, properly registered in reference to and properly bonded to layer 2, was demonstrated to be the feature that resulted in completely eliminating leakage to the protected sites.

Prototypes of first embodiment achieved 100% efficacy in preventing water intrusion into protected sites, even when outer waterproof layers failed and when both "inner bandages" and "outer bandages" had induced seal flaws. The outer absorbent layer reliably kept sweat and external water intrusion from the inner bandage pad even when saturated.

Advantages:

Accordingly, from the above description and testing results, one or more aspects of the embodiments provide advantages, including, but not limited to the following:

Reliably protects a site or dressing during showering or bathing even if the adhesive to skin or other seal leaks.

The design provides a novel mechanism by which leakage is prevented from reaching protected sites.

Protects edges and integrity of dressing or inner bandage layer even in the presence of water intrusion.

High-strength adhesives not required for perfect seals since the design is insensitive to seal leaks, which eases removal of the bandage Design is compatible with other overall configurations to provide protection for different applications or circumstances, such as use as a waterproof bandage, waterproof cast cover, or waterproof site dressing cover, among other uses.

Can be made in different shapes to achieve a configuration best suited for a target application Outer bandage can be separately removable and/or be reusable to increase the life of the inner bandage Reusable layers are possible to reduce waste.

Can be constructed from easily obtainable materials at relatively low cost.

Less sensitive to user error in application, while providing more reliable protection as compared to existing art.

We claim:

1. An apparatus comprising:
   a first bandage component comprising a first waterproof layer having a first waterproof layer shape;
   a second bandage component comprising a second waterproof layer having a second waterproof layer shape;
   a third bandage component comprising a first absorbent layer having a first absorbent layer shape;
   a fourth bandage component comprising a second absorbent layer having a second absorbent layer shape;
   wherein the second waterproof layer having the second waterproof layer shape is disposed over and overlaps the second absorbent layer having the second absorbent layer shape, which in turn, is disposed over and overlaps all edges of the first waterproof layer having the first waterproof layer shape, which in turn, is disposed over and overlaps the first absorbent layer having the first absorbent layer shape;
   wherein the second absorbent layer is used to absorb or attract a liquid such that the liquid does not infiltrate the edges of the first waterproof layer;
   a bonding layer located between the edges of the first waterproof layer having the first waterproof layer shape and the second absorbent layer having the second absorbent layer shape, wherein the second absorbent layer having the second absorbent layer shape is adhered to the first waterproof layer having the first waterproof layer shape;
   wherein a combination of the bonding layer located at the edges of the first waterproof layer and the second absorbent layer which is disposed and overlaps the edges of the first waterproof layer are configured to prevent a liquid intrusion.

2. The apparatus of claim 1 wherein the first absorbent layer absorbs a fluid including at least one of water, sweat or blood.

3. The apparatus of claim 1 wherein at least one of the first waterproof layer shape, the second waterproof layer shape, the first absorbent layer shape, or the second absorbent layer shape comprises at least one of: geometric or organic shapes, polygons, circles, rings, ovals or shapes that are tubular.

4. The apparatus of claim 1 wherein at least one of the first waterproof layer, the second waterproof layer, the first absorbent layer, or the second absorbent layer has a lengthwise slit.

5. The apparatus of claim 1 wherein one or more of the first bandage component, the second bandage component, the third bandage component, or the fourth bandage component is wrapped around an appendage.

6. The apparatus of claim 5 wherein one or more of the first bandage component, the second bandage component, the third bandage component, or the fourth bandage component has an end cap.

7. The apparatus of claim 6 wherein the end cap is made of a waterproof material.

8. The apparatus of claim 6 wherein the end cap is made of the same materials as at least one of the first bandage component, the second bandage component, the third bandage component, or the fourth bandage component.

9. The apparatus of claim 5 wherein one or more of the first bandage component, the second bandage component, the third bandage component, or the fourth bandage component is held in place using a tightening or securing mechanism.

10. The apparatus of claim 1 wherein at least one of the first waterproof layer, the second waterproof layer, the first absorbent layer, or the second absorbent layer is configured to be replaced.

11. The apparatus of claim 1 wherein at least one of the first waterproof layer, the second waterproof layer, the first absorbent layer, or the second absorbent layer is made of a at least one of a biodegradable material, a non-rigid material, or a non-rigid film.

12. The apparatus of claim 1 wherein one or more additional outer bandage layers may be applied over the second bandage component comprising the second waterproof layer.

13. The apparatus of claim 1 wherein at least one of the first absorbent layer or the second absorbent layer is made of fiber or cloth.

14. The apparatus of claim 1 wherein the bonding layer includes at least one of:
an adhesive,
a non-adhesive,
a full seal,
a pressure seal,
a non-full seal,
one or more strips of the adhesive or of the non-adhesive,
one or more adhesive strips, or
one or more compression straps.

15. The apparatus of claim 1 wherein the first waterproof layer and the second waterproof layer each include an adhesive.

16. The apparatus of claim 1 wherein
the second absorbent layer protects the first bandage component comprising the first waterproof layer after the second absorbent layer is saturated.

17. The apparatus of claim 1 wherein at least one of the second waterproof layer or the second absorbent layer is made of a washable or reusable material.

18. A method for manufacture of an apparatus, comprising:
providing a first bandage component comprising a first waterproof layer having a first waterproof layer shape;
providing a second bandage component comprising a second waterproof layer having a second waterproof layer shape;
providing a third bandage component comprising a first absorbent layer having a first absorbent layer shape;
providing a fourth bandage component comprising a second absorbent layer having a second absorbent layer shape;
wherein the second waterproof layer having the second waterproof layer shape is disposed over and overlaps, at least in part, the second absorbent layer having the second absorbent layer shape, which in turn, is disposed over and overlaps all edges of the first waterproof layer having the first waterproof layer shape, which in turn, is disposed over and overlaps, at least in part, the first absorbent layer having the first absorbent layer shape;
wherein the second absorbent layer is used to absorb or attract a liquid such that the liquid does not infiltrate the edges of the first waterproof layer;
providing a bonding layer located between the edges of the first waterproof layer having the first waterproof layer shape and the second absorbent layer having the second absorbent layer shape, wherein the second absorbent layer having the second absorbent layer shape is adhered to the first waterproof layer having the first waterproof layer shape;
wherein a combination of the bonding layer located at the edges of the first waterproof layer and the second absorbent layer which is disposed and overlaps the edges of the first waterproof layer are configured to prevent a liquid intrusion.

19. The apparatus of claim 1, wherein at least one of:
the first absorbent layer differs from the second absorbent layer;
the second absorbent layer is made of fiber or cloth;
the first waterproof layer includes at least one of a catheter line cover or a PICC line cover; or
the second absorbent layer is configured to wick away the liquid from the first waterproof layer.

* * * * *